United States Patent [19]
Foshee et al.

[11] Patent Number: 5,342,391
[45] Date of Patent: Aug. 30, 1994

[54] CLEANABLE ENDOSCOPIC SURGICAL INSTRUMENT

[75] Inventors: David L. Foshee, Cary; Robert S. Lynch, Durham, both of N.C.

[73] Assignee: Linvatec Corporation, Largo, Fla.

[21] Appl. No.: 957,336

[22] Filed: Oct. 6, 1992

[51] Int. Cl.⁵ ............................................. A61B 17/32
[52] U.S. Cl. ..................................... 606/205; 606/52
[58] Field of Search ............................. 606/46–52, 606/138–144, 205–209, 170

[56] References Cited

U.S. PATENT DOCUMENTS

| | | | |
|---|---|---|---|
| 2,113,246 | 4/1938 | Wappler | 606/205 |
| 4,084,594 | 4/1978 | Mosior | 606/170 |
| 4,896,678 | 1/1990 | Ogawa | 606/170 |
| 5,147,357 | 9/1992 | Rose et al. | 606/51 |

Primary Examiner—Stephen C. Pellegrino
Assistant Examiner—M. Peffley
Attorney, Agent, or Firm—Gene Warzecha

[57] ABSTRACT

An endoscopic surgical instrument which is able to be disassembled in order to facilitate cleaning of the instrument or replacement of certain components. The instrument comprises a handle portion at the proximal end of an elongated rotatable shaft, the handle portion including a pair of handles biased into a normally open position and movable between the normally open position and a closed position. Movement of the handles within the normal range serves to axially move an elongated working element situated within the hollow interior of the elongated sleeve, the proximal end of the working element shaft having a stud adapted to be received within a stud recess in one of the handles. The stud recess has a front slotted wall and an open top end. A spring means is provided in order to bias the handles during normal operation and a latch means is provided in order to disengage the spring. When the spring is disengaged, the handles may be moved beyond their normal range of motion so they may be placed into a disassembly position in which the stud on the proximal end of the working element may be pulled distally from the stud recess in order to enable the working element to be removed from the instrument.

3 Claims, 3 Drawing Sheets

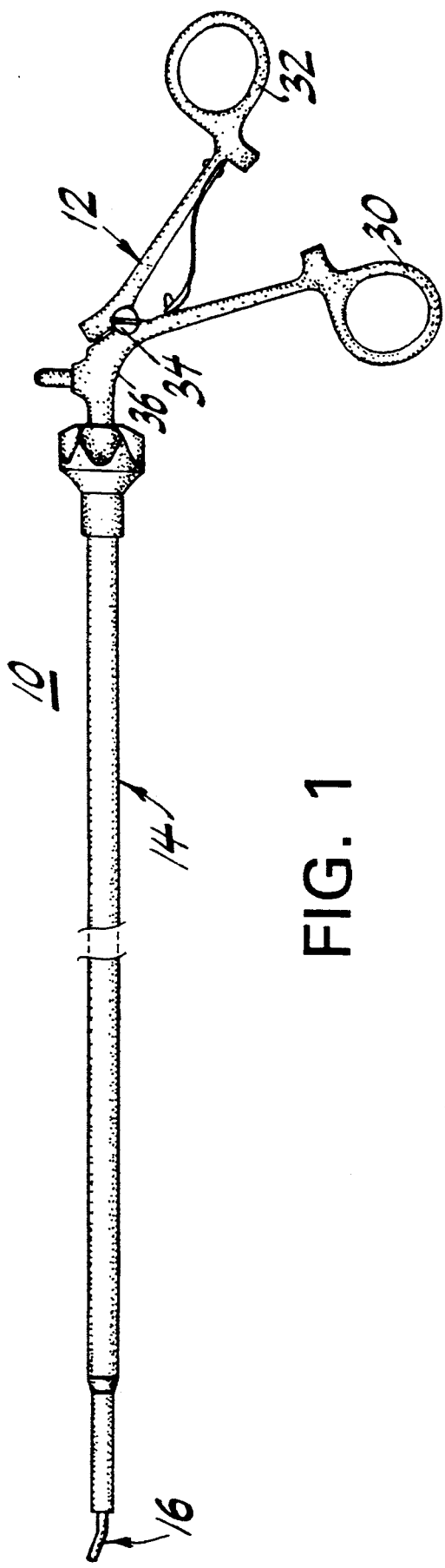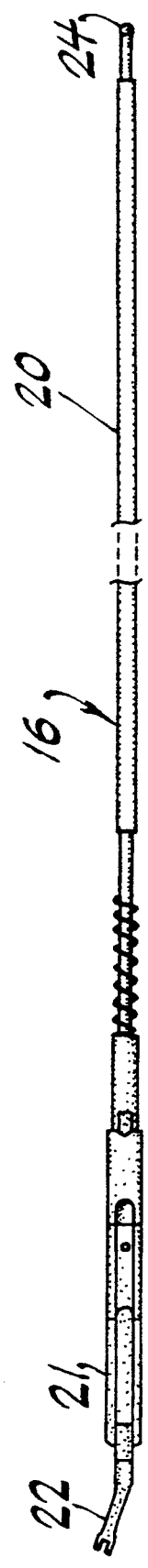

CLEANABLE ENDOSCOPIC SURGICAL INSTRUMENT

BACKGROUND OF THE INVENTION

1. Field of the Invention

This invention relates generally to surgical instruments. More particularly, this invention relates to endoscopic surgical instruments having component parts which may be disassembled in order to clean the instrument prior to reuse.

2. Description of the Prior Art

Endoscopic surgical procedures require the use of elongated instruments having some handle or control means at the proximal end and a variety of different working elements or instruments at the distal end to facilitate such activities as cutting, gripping, applying ligating clips, etc. These instruments are inserted through a cannula to enable the surgeon to place the instrument at a working site within the body, the site being viewed by a camera through an endoscope inserted through another portal in the body.

Since endoscopic instruments are often reused, they must be cleaned and sterilized between each use. The current designs of reusable endoscopic instruments do not always facilitate such cleaning and sterilization. One known prior art manner of cleaning reusable endoscopic instruments is disclosed in U.S. patent application Ser. No. 07/913,852, assigned to the assignee hereof. The instrument shown in this application incorporates a rotatable elongated working element having a check valve near the proximal end adapted for flushing the interior of the instrument during the cleaning process.

It is also known in the prior art to disassemble surgical instruments for cleaning purposes although the disassembly of endoscopic surgical instruments has often been either cumbersome or insufficient to assure adequate cleaning of the instrument.

It is an object of the present invention to produce an endoscopic surgical instrument in which selected portions of the instrument may be disassembled to facilitate cleaning prior to reuse.

It is also an object of this invention to produce an endoscopic surgical instrument having a minimum number of parts which need to be disassembled in order to facilitate the cleaning process.

SUMMARY OF THE INVENTION

These and other objects of the invention are achieved by the preferred embodiment disclosed herein which comprises an endoscopic surgical instrument having a pair of pivotably connected ring handles, an elongated tubular shaft secured to one of the ring handles and a working element slidably and removably mounted within the elongated tubular shaft. The proximal end of the working element is provided with a stud which is received in a stud recess in the top end of the other of the ring handles. The stud recess has a narrow distal slot and an open top and is adapted to enable the stud (and consequently the working element) to be moved axially within the elongated tubular shaft within a normal linear range of motion in response to movement of the ring handles within a normal pivotal range of motion. A latch means is provided in order to enable the handles to be moved beyond their normal range of motion into a disassembly position in which the stud at the proximal end of the working element is removable through the open top of the stud recess in order to enable the working element to be removed from the handle and elongated tubular shaft portions of the instrument.

BRIEF DESCRIPTION OF THE DRAWINGS

FIG. 1 is a side elevation view of an endoscopic instrument constructed in accordance with the principles of this invention.

FIG. 2 is a side elevation view of a portion of the instrument shown in FIG. 1.

DESCRIPTION OF THE PREFERRED EMBODIMENT

Figures 3, 4:
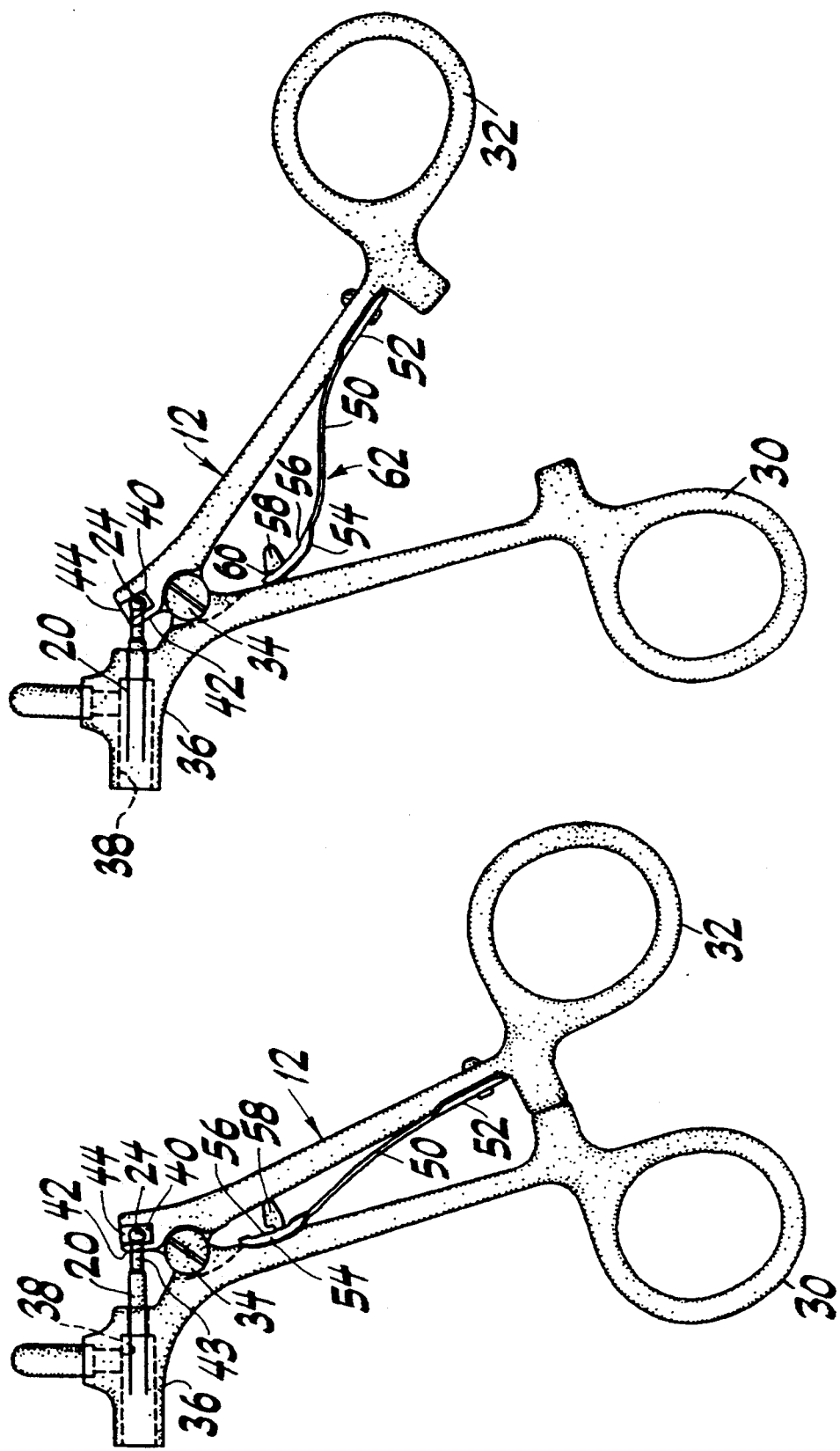
FIG. 3 is a side elevation view partly in cross-section of a portion of the handle of the instrument of FIG. 1 shown in a closed position.
FIG. 4 is a view of the handles shown in FIG. 3 showing them in a normal, biased open position.

Referring now to FIG. 1, there is shown an endoscopic instrument 10 constructed in accordance with the principles of this invention. Instrument 10 comprises a handle portion 12, an elongated and rotatable hollow sleeve portion 14 and a working element portion 16.

Working element portion 16, best seen in FIG. 2, comprises an elongated shaft 20 having an instrument 21 at its distal end and a stud 24 at its proximal end. The operation of instrument 21 need not be explained in detail in order to obtain an understanding of the present invention, however, some minor explanation will be helpful. As will be understood below, working element 16 moves longitudinally with respect to elongated shaft 14 in response to the motion of handle portion 12. Instrument 21 may be any one of a variety of instruments such as ligating clip applier jaws, forceps, scissors, etc. The relative motion of instrument 21 and the distal end of shaft 14 creates an interaction which can activate the component parts of instrument 21. In the embodiment shown, instrument 21 is a pair of ligating clip applier jaws 22 which are used to apply ligating clips in a conventional manner and are open when shaft 20 is in its distal-most position relative to sleeve 14. When shaft 20 is moved proximally relative to sleeve 14, the distal end of the sleeve cooperates with the outer sides of the jaws (not shown) to close the jaws together in a conventional manner. The motion of working element portion 16 is controlled by handle portion 12 as will be understood below. While the preferred embodiment of the invention shown herein is a ligating clip applier, it will be understood that numerous other working elements may be incorporated with the invention.

Handle portion 12 comprises a pair of ring handles 30 and 32 pivotably connected at 34. Ring handle 30 has a top end base 36 provided with a bore 38 axially aligned with that of sleeve 14. Rotatably secured to the proximal side of handle base 36 is the proximal end of sleeve 14. The hollow interior of sleeve 14 is aligned with bore 38 in order to receive working element 16. Stud 24 at the proximal end of working element 16 is received in stud recess 40 formed in the top end of ring handle 32. The proximal side 42 of stud recess 40 is provided with a vertically oriented slot (not shown) which is wide enough to receive the thinned shaft portion 43 of shaft 20 but too small to allow stud 24 to pass therethrough. Recess 40 has an open top end 44 which is, however, large enough to allow stud 24 to pass therethrough. In normal operation of handle 12, however, stud 24 is normally pressed against the proximally facing surface of wall 42 (i.e. the interior of recess 40) during the normal range of motion of ring handles 30 and 32. Stud 24 may have a variety of shapes provided it is able to be retained in recess 40 and, if rotation of shaft 14 is desired, further provided that the stud be rotatable within the recess.

Figure 5:
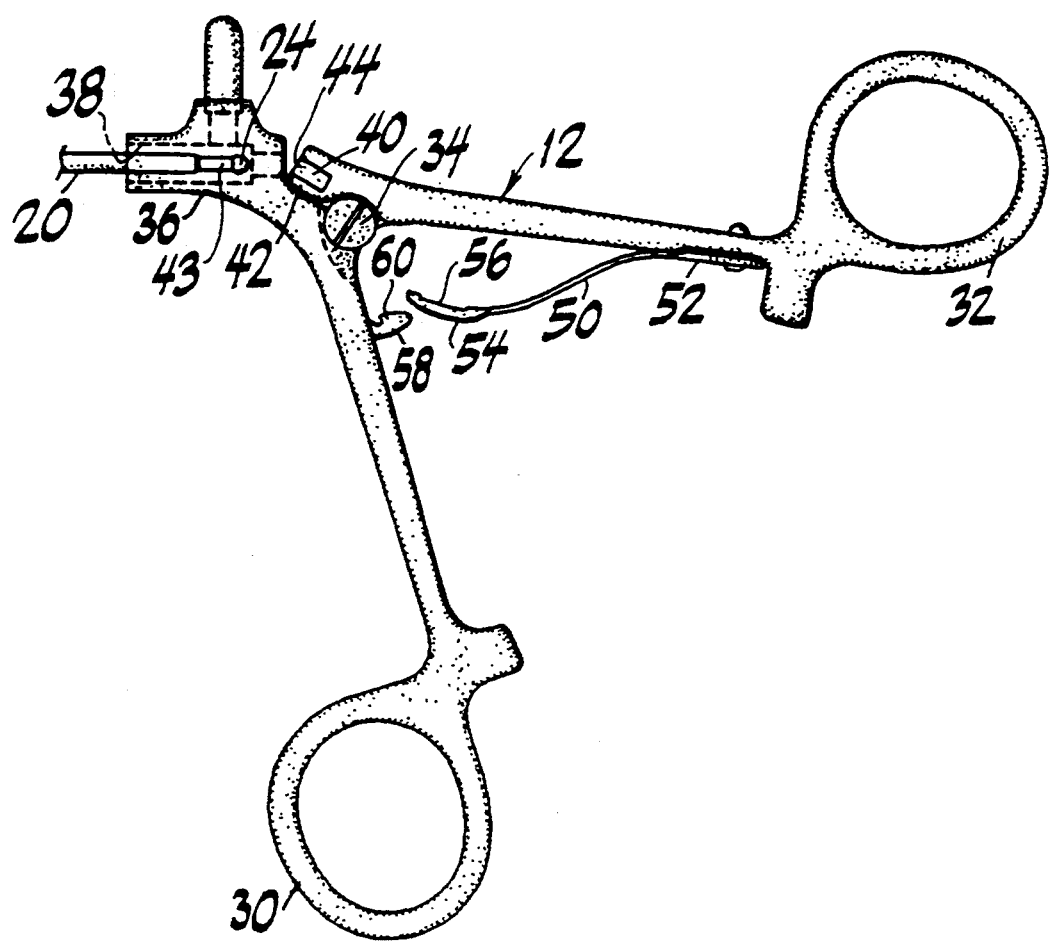
FIG. 5 is a view of the handles shown in FIGS. 3 and 4 shown in an extended, disassembly position.

Leaf spring member 50 has one end 52 fixedly secured to handle 32 and the other end 54 detachably secured to handle 30. Leaf spring end 54 has a slot 56 adapted to engage latching post 58 and provides the normally open biasing force between the ring handles. During the normal range of motion between the open position of the handles shown in FIG. 4 and the closed position shown in FIG. 3, slot 56 moves relative to post 58 as handle 32 moves relative to handle 30. During this entire range of motion leaf spring end 54 is pressed against handle 30 except at the open position where the distal end of slot 56 is prevented from becoming disengaged from post 58 by tooth 60. By manually pressing leaf spring 50 upward in the direction shown by arrow 62, a user may disengage leaf spring end 54 from latch 58, thereby enabling handles 30 and 32 to be opened beyond the normal open position into a disassembly position shown in FIG. 5. When the handles are so positioned, the top opening 44 of stud recess 40 is oriented in a more distally facing position enabling stud 24 to be pulled past to top of the vertical slot (not shown) in wall 42 and out of recess 40, thereby enabling the entire working element 16 to be removed from handle portion 12 and out through the distal end of sleeve portion 14. This disassembly facilitates cleaning the instrument by enhancing access to working element 16 and the interior channels of sleeve 14 and bore 38. This disassembly also facilitates the use of a reusable handle portion and sleeve portion with a disposable working element portion.

It will be understood by those skilled in the art that numerous improvements and modifications may be made to the preferred embodiment of the invention disclosed herein without departing from the spirit and scope thereof.

What is claimed is:

1. An endoscopic surgical instrument comprising:
    a handle portion at one end of said instrument, said handle portion having a pair of lever arms pivotably connected together to move relative to each other within a normal range of motion;
    a tubular shaft portion having a proximal end and a distal end, said proximal end secured to said handle portion;
    an elongated working element portion adapted to be received within said tubular shaft portion, said working element portion having a working means at its distal end and a securing means at its proximal end for securing said working element portion to said handle, said working element portion adapted to reciprocate longitudinally within said shaft in response to motion of said lever arms relative to each other;
    leaf spring means interposed between said lever arms to bias same to a normally open position, the bias of said leaf spring means able to be overcome by a user moving said lever arms together, said leaf spring means comprising a leaf spring connected at one end thereof to one of said lever arms and at the other end thereof to the other of said lever arms to thereby restrict the motion of said lever arms relative to each other to be within a predetermined range of motion, said other end connection being releasable from said other of said lever arms in order to disconnect said leaf spring from said other of said lever arms to thereby enable said lever arms to be pivoted away from each other beyond their normal open position;
    releasable securing means at the top end of one of said lever arms for releasably engaging said proximal end of said working element portion, said releasable securing means acting to engage said working element portion during said normal range of motion of said lever arms and acting to enable said proximal end to be disengaged from said one of said lever arms upon placement thereof into a disassembly position beyond said normal range of motion.

2. An endoscopic surgical instrument comprising:
    a handle means comprising a pair of handle portions movable relative to one another between a closed position and an open position;
    biasing means for biasing said handle portions to a normally open position;
    releasable latch means interposed between said handle portions for selectively latching said biasing means to, in normal use, prevent motion of said handle portions beyond a normal range of motion between said normally open position and a normally closed position;
    an elongated tubular shaft having a distal end and a proximal end, the latter secured to said handle means;
    an elongated working element slidably and removably mounted within said shaft, said working element having a distal end and a proximal end;
    means for releasably securing said handle means to said proximal end of the working element, said securing means adapted to enable said working element to be disengaged from said securing means and pulled distally from the distal end of said tubular shaft when said releasable latch means is actuated to enable motion of said handle portions beyond said normal range of motion; and
    means for selectively unlatching said releasable latch means to enable motion of said handle portions beyond said normal range of motion and into a predetermined disassembly position wherein said working element may be disengaged.

3. An endoscopic surgical instrument according to claim 2 wherein said means for selectively unlatching said latching means operates to enable said handle portions to move beyond said normally open position.

* * * * *